(12) United States Patent
Matsui et al.

(10) Patent No.: US 10,484,626 B2
(45) Date of Patent: Nov. 19, 2019

(54) GAIN ADJUSTMENT UNIT, RECORDING MEDIUM HOLDING GAIN ADJUSTMENT PROGRAM, ENDOSCOPE AND ENDOSCOPE APPARATUS

(71) Applicant: OLYMPUS CORPORATION, Tokyo (JP)

(72) Inventors: Yasunori Matsui, Hino (JP); Shinji Yamashita, Tachikawa (JP); Yuzuru Tanabe, Niiza (JP); Yuta Matsuno, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 132 days.

(21) Appl. No.: 15/678,259

(22) Filed: Aug. 16, 2017

(65) Prior Publication Data

US 2017/0374301 A1 Dec. 28, 2017

Related U.S. Application Data

(63) Continuation of application No. PCT/JP2016/079792, filed on Oct. 6, 2016.

(30) Foreign Application Priority Data

Jan. 12, 2016 (JP) ................................ 2016-003899

(51) Int. Cl.
*H04N 5/365* (2011.01)
*H04N 5/378* (2011.01)
(Continued)

(52) U.S. Cl.
CPC ......... *H04N 5/351* (2013.01); *A61B 1/00009* (2013.01); *A61B 1/04* (2013.01);
(Continued)

(58) Field of Classification Search
CPC ........... H04N 2005/2255; H04N 5/378; H04N 5/243; H04N 5/2354; H04N 5/2352;
(Continued)

(56) References Cited

U.S. PATENT DOCUMENTS

2003/0160865 A1 8/2003 Takahashi
2009/0256934 A1 10/2009 Usami et al.
(Continued)

FOREIGN PATENT DOCUMENTS

EP 2 567 652 A1 3/2013
JP 2003-319905 A 11/2003
(Continued)

OTHER PUBLICATIONS

International Search Report dated Dec. 20, 2016 issued in PCT/JP2016/079792.
(Continued)

*Primary Examiner* — Jared Walker
*Assistant Examiner* — Samuel D Fereja
(74) *Attorney, Agent, or Firm* — Scully, Scott, Murphy & Presser, P.C.

(57) ABSTRACT

A gain adjustment unit calculates a total sum of analog gains on a way from photoelectric conversion output of an image pickup device to input of an analog/digital conversion circuit with use of picked-up images provided from the analog/digital conversion circuit, the analog/digital conversion circuit being configured to convert an output of an analog processing section into a digital signal, the analog processing section being configured to transmit and amplify an image pickup signal from the image pickup device, the image pickup device being provided at an insertion portion of an endoscope, and determines, as an adjustment gain, a difference between a target value of a total sum of gains and the total sum of the analog gains, and output information.

8 Claims, 4 Drawing Sheets

(51) Int. Cl.
*A61B 1/04* (2006.01)
*H04N 5/351* (2011.01)
*G02B 23/24* (2006.01)
*A61B 1/00* (2006.01)
*A61B 1/045* (2006.01)

(52) U.S. Cl.
CPC .............. *A61B 1/045* (2013.01); *G02B 23/24* (2013.01); *H04N 5/365* (2013.01); *H04N 5/378* (2013.01)

(58) Field of Classification Search
CPC .... H04N 5/355; H04N 5/23203; H04N 5/361; H04N 17/002; H04N 5/2256; H04N 5/2353; H04N 5/2355; H04N 5/3559; H04N 5/357; H04N 5/363; H04N 5/367; H04N 5/374; H04N 5/3745; H04N 1/193; H04N 5/20; H04N 5/217; H04N 5/232; H04N 5/235; H04N 5/32; H04N 5/335; H04N 5/351; H04N 5/3575; H04N 5/372; H04N 5/37455; H04N 5/3765; H04N 7/183; H04N 9/045; H04N 9/735; H04N 1/1013; H04N 1/1017; H04N 1/40056; H04N 1/4076; H04N 3/1568; H04N 5/148; H04N 5/202; H04N 5/21; H04N 5/2251; H04N 5/2253; H04N 5/23209; H04N 5/23212; H04N 5/23229; H04N 5/23241; H04N 5/23245; H04N 5/2348; H04N 5/23254; H04N 5/23258; H04N 5/23267; H04N 5/23283; H04N 5/2351; H04N 5/33; H04N 5/3355; H04N 5/341; H04N 5/343; H04N 5/3454; H04N 5/35545; H04N 5/35581; H04N 5/3572; H04N 5/365; H04N 5/369; H04N 5/3692; H04N 5/3698; H04N 5/3741; H04N 5/37457; H04N 7/185; H04N 9/04; H04N 9/07; H04N 9/642; A61B 1/00009; A61B 1/045; A61B 1/0638; A61B 1/043; A61B 1/0646; A61B 1/04; A61B 5/0071; A61B 5/0084; A61B 1/042; A61B 1/05; A61B 1/00006; A61B 1/00059; A61B 1/051; A61B 1/06; A61B 1/00004; A61B 1/00011; A61B 1/00018; A61B 1/041; A61B 1/053; A61B 1/063; A61B 1/00045; A61B 1/0005; A61B 1/00057; A61B 1/00186; A61B 5/726; A61B 18/20; A61B 1/00016; A61B 1/00039; A61B 1/00087; A61B 1/00096; A61B 1/00105; A61B 1/00165; A61B 1/00172; A61B 1/00188; A61B 1/018; A61B 1/0653; A61B 1/0661; A61B 1/0669; A61B 1/0676; A61B 1/0684; A61B 1/07; A61B 1/128; A61B 2018/00982; A61B 2018/2025; A61B 5/0059; A61B 5/024; A61B 6/52; G02B 23/24; G02B 23/2469; G02B 23/2484; G02B 23/26; G02B 23/2423; G02B 23/2461; G02B 23/2476; G02B 21/0084

See application file for complete search history.

(56) References Cited

U.S. PATENT DOCUMENTS

2013/0041220 A1* 2/2013 Kutsuma ............ A61B 1/00009
                                                    600/109
2014/0309491 A1 10/2014 Karasawa

FOREIGN PATENT DOCUMENTS

| JP | 2008-093174 A | 4/2008 |
| JP | 2009-106442 A | 5/2009 |
| JP | 2014-204892 A | 10/2014 |

OTHER PUBLICATIONS

Extended Supplementary European Search Report dated Oct. 5, 2018 in European Patent Application No. 16 88 5000.6.

* cited by examiner

GAIN ADJUSTMENT UNIT, RECORDING MEDIUM HOLDING GAIN ADJUSTMENT PROGRAM, ENDOSCOPE AND ENDOSCOPE APPARATUS

CROSS REFERENCE TO RELATED APPLICATION

This application is a continuation application of PCT/JP2016/079792 filed on Oct. 6, 2016 and claims benefit of Japanese Application No. 2016-003899 filed in Japan on Jan. 12, 2016, the entire contents of which are incorporated herein by this reference.

BACKGROUND OF THE INVENTION

1. Field of the Invention

The present invention relates to a gain adjustment unit, a recording medium holding a gain adjustment program, an endoscope, and an endoscope apparatus that make it possible to adjust variation of an analog gain to realize high image quality.

2. Description of the Related Art

In recent years, an image pickup apparatus that uses an image pickup device such as a CCD sensor and a CMOS sensor has been used in various fields. For example, in a medical field, an electronic endoscope apparatus using an image pickup device is employed as an endoscope apparatus used for diagnosis and medical treatment using treatment instruments in some cases. An electronic endoscope has an elongated insertion portion on distal end side, and the image pickup device is provided at a distal end of the insertion portion. In addition, a connector for connection with a video processor is provided on proximal end side of the endoscope. An image pickup signal obtained by the endoscope is supplied to the video processor through the connector, and an endoscope image is accordingly generated by the video processor.

In recent years, image processing by the video processor has been digitalized, and an output of the image pickup device is converted into a digital signal, and the digital signal is used in the image processing. In this case, an output level of photoelectric conversion output by the image pickup device is relatively small. Therefore, an analog output signal of the image pickup device is sufficiently amplified, and the amplified signal is then provided to an analog/digital convertor to be converted into a digital signal. This makes it possible to generate an endoscope image with sufficient brightness by the video processor and to display the clear endoscope image.

Japanese Patent Application Laid-Open Publication No. 2008-93174 discloses an endoscope apparatus that adjusts a gain of an AGC circuit so as to obtain appropriate brightness of an image.

Incidentally, in the endoscope, the output signal of the image pickup device provided at the distal end of the insertion portion is electrically transmitted through a cable to an electric substrate incorporated in a connector portion on proximal end side of the insertion portion (hereinafter, referred to as an in-connector substrate). The cable that electrically transmits the output signal of the image pickup device has a relatively long length, which causes the output signal of the image pickup device to attenuate relatively largely. Therefore, it is necessary to amplify the output signal of the image pickup device with a relatively large gain until the output signal of the image pickup device is supplied to an analog/digital converter mounted on the in-connector substrate.

SUMMARY OF THE INVENTION

A gain adjustment unit according to an aspect of the present invention includes: an analog total gain calculation section configured to calculate a total sum of analog gains on a way from photoelectric conversion output of an image pickup device to input of an analog/digital conversion circuit with use of picked-up images provided from the analog/digital conversion circuit, the analog/digital conversion circuit being configured to convert an output of an analog processing section into a digital signal, the analog processing section being configured to transmit and amplify an image pickup signal from the image pickup device, the image pickup device being provided at an insertion portion of an endoscope; and an adjustment gain calculation section configured to determine, as an adjustment gain, a difference between a target value of a total sum of gains on the way from the photoelectric conversion output of the image pickup device to the input of the analog/digital conversion circuit and the total sum of the analog gains, and output information of the adjustment gain to adjust an analog gain of the endoscope.

In addition, an endoscope according to an aspect of the present invention includes: a recording section configured to record information of the adjustment gain that is provided from the gain adjustment unit; and a digital amplifier configured to add the adjustment gain to an output of the analog/digital conversion circuit, on a basis of the information of the adjustment gain.

Further, an endoscope according to another aspect of the present invention includes: a recording section configured to record information of the adjustment gain that is provided from the gain adjustment unit; and an analog gain control section configured to control a gain of the analog processing section to add the adjustment gain to the total sum of the analog gains, on a basis of the information of the adjustment gain.

Furthermore, an endoscope apparatus according to an aspect of the present invention includes: the endoscope; and a video processor that receives an output of the endoscope and performs predetermined image processing on the output, in which the video processor includes the gain adjustment unit.

Moreover, a recording medium according to an aspect of the present invention has a gain adjustment program, and the gain adjustment program causes a computer to execute: a step of calculating a total sum of analog gains on a way from photoelectric conversion output of an image pickup device to input of an analog/digital conversion circuit with use of a picked-up image based on an output of the image pickup device at bright time and a picked-up image based on an output of the image pickup device at dark time among picked-up images provided from the analog/digital conversion circuit, the analog/digital conversion circuit being configured to convert an output of an analog processing section into a digital signal, the analog processing section being configured to transmit and amplify an image pickup signal from the image pickup device, the image pickup device being provided at an insertion portion of an endoscope; and a step of determining, as an adjustment gain, a difference between a target value of a total sum of gains on the way from the photoelectric conversion output of the image pickup device to the input of the analog/digital conversion circuit and the total sum of the analog gains, and outputting information of the adjustment gain to adjust an analog gain of the endoscope.

DETAILED DESCRIPTION OF THE PREFERRED EMBODIMENT(S)

An embodiment of the present invention is described in detail below with reference to drawings.

First Embodiment

Figure 1:
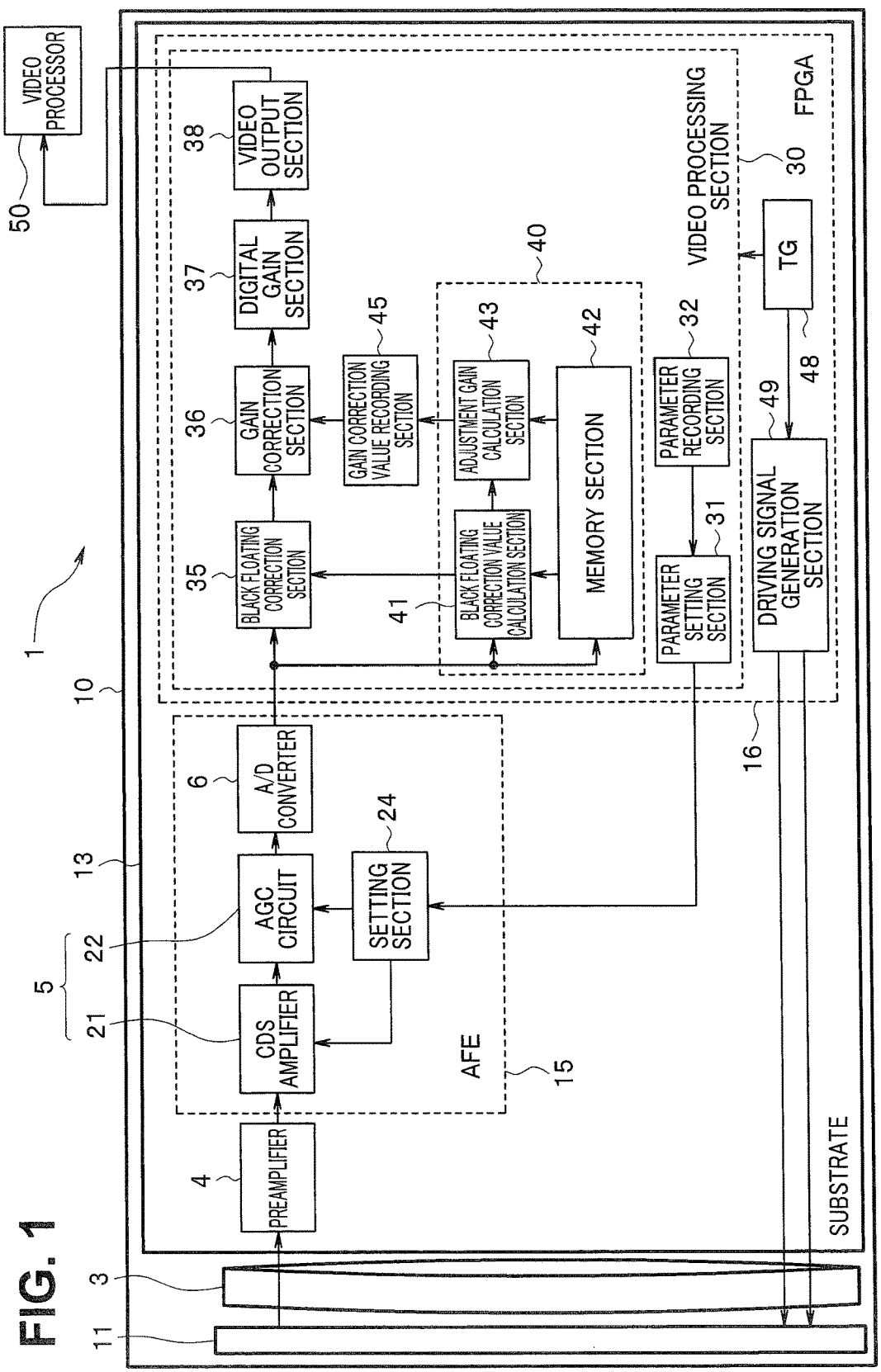
FIG. 1 is a block diagram illustrating an endoscope apparatus including an endoscope that includes a built-in gain adjustment unit according to a first embodiment of the present invention.

FIG. 1 is a block diagram illustrating an endoscope apparatus including an endoscope that includes a built-in gain adjustment unit according to a first embodiment of the present invention.

Figure 2:
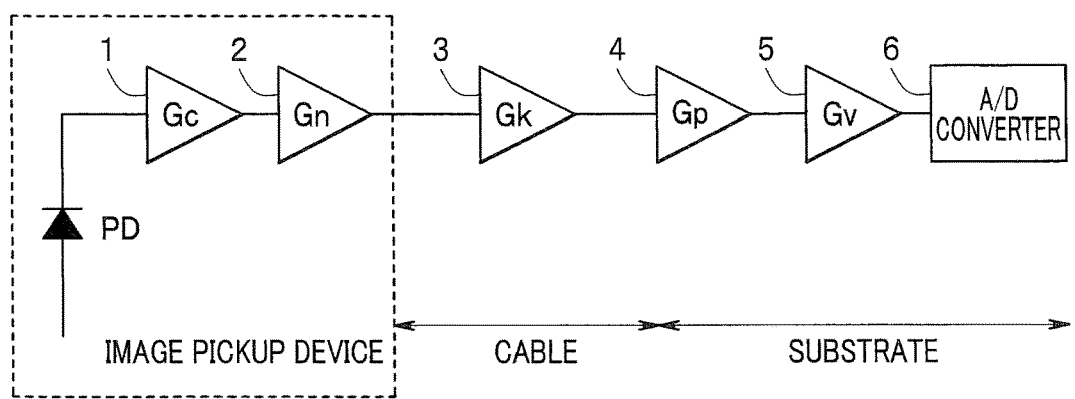
FIG. 2 is an explanatory diagram illustrating generation sources of respective analog gains that exist on a way from an image pickup device to an A/D converter.
Figure 3:
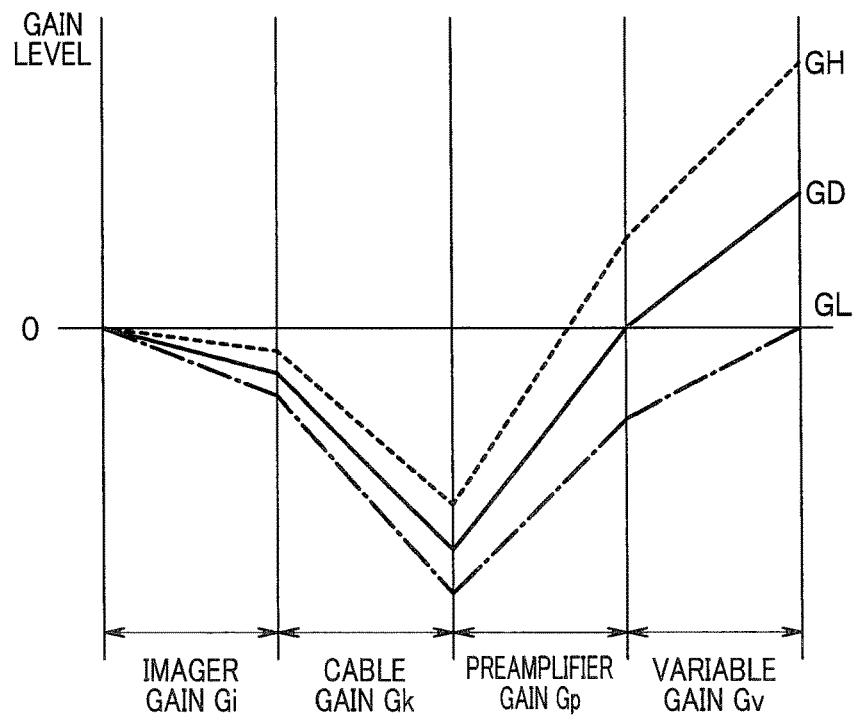
FIG. 3 is a graph illustrating variation of each of the analog gains of FIG. 2, in which a horizontal axis indicates each stage of the gain generation sources and a vertical axis indicates a gain.

First, variation of a gain (an analog gain) that occurs in an analog manner until a photoelectric conversion output of an image pickup device is provided to an analog/digital converter (A/D converter), with reference to FIG. 2 and FIG. 3. FIG. 2 is an explanatory diagram illustrating generation sources of respective analog gains that exist on the way from the image pickup device to the A/D converter. FIG. 3 is a graph illustrating variation of each of the analog gains of FIG. 2, in which a horizontal axis indicates each stage of the gain generation sources and a vertical axis indicates a gain.

The endoscope includes the image pickup device that is disposed at a distal end of an insertion portion at a distal end of the endoscope, and an output signal of the image pickup device (an image pickup signal) is transmitted to proximal end side of the endoscope through a cable. For example, the A/D converter is provided in a connector of a universal cable that is connected to the proximal end side of the endoscope or in a video processor that is connected to the endoscope through the connector. The A/D converter converts an analog image pickup signal transmitted through the cable, into a digital image pickup signal.

FIG. 2 illustrates an example of a case where the generation sources of the respective analog gains are a floating diffusion section 1, an imager built-in amplifier 2, a cable 3, a preamplifier 4, and a variable amplifier 5 (hereinafter, simply referred to as analog amplifiers).

In FIG. 2, the image pickup device includes a photodiode PD. The photodiode PD generates electrons through photoelectric conversion. The electrons are converted into a voltage signal by the floating diffusion section 1. A gain in the floating diffusion section 1 is referred to as a conversion gain Gc. In addition, the imager built-in amplifier 2 is incorporated in the image pickup device. A gain in the imager built-in amplifier 2 is referred to as an imager internal gain Gn. The image pickup signal is transmitted through the cable 3. A gain (attenuation) by resistance (cable resistance), end part resistance, and matching resistance of the cable 3 is referred to as a cable gain Gk. Typically, the image pickup signal transmitted through the cable 3 is amplified by the preamplifier 4 and the variable amplifier 5 in a substrate, for example, before the image pickup signal is supplied to the A/D converter 6 disposed inside the substrate. The preamplifier 4 adds, to the image pickup signal, a preamplifier gain Gp to supply a signal with high level of S/N necessary for the circuit inside the substrate. The variable amplifier 5 adds, to the image pickup signal, a variable gain Gv to set the image pickup signal to a level corresponding to an input range of the A/D converter.

The conversion gain Gc and the imager internal gain Gn (hereinafter, both correctively referred to as an imager gain Gi) are varied for each image pickup device, for example, depending on a process even in the same standard. In addition, the cable gain Gk is also varied for each cable due to, for example, variation of impedance even when the cables have the same diameter, the same line length, and the same configuration. Further, in the case where the amplifiers inside the substrate are configured in an analog manner, the preamplifier gain Gp and the variable gain Gv are also varied for each amplifier even in the same standard.

FIG. 3 illustrates the variation of the gains. A solid line in FIG. 3 indicates design values of the respective gains. When the gain at the input of the floating diffusion section 1 is regarded as a reference, each of the imager gain Gi and the cable gain Gk has a negative value, and the photoelectric conversion output accordingly attenuates until being supplied to the preamplifier 4. The image pickup signal is amplified by the preamplifier 4 and the variable amplifier 5, and the amplified image pickup signal is provided to the A/D converter 6. A gain (a target value) at the input of the A/D converter 6 becomes a positive value GD. The value GD is a design value, and the value of the gain is actually varied.

A dashed line in FIG. 3 illustrates change of the gain in the case where the gain in each of the analog amplifiers is varied in a positive direction. An alternate long and short dash line in FIG. 3 illustrates change of the gain in the case where the gain in each of the analog amplifiers is varied in a negative direction. As illustrated in FIG. 3, variation is added for each stage, and an estimated maximum value of the variation of the gain at the input of the A/D converter 6 is GH, and an estimated minimum value is GL.

In design, the total sum of the gains in FIG. 3, namely, the total sum of the analog gains (hereinafter, referred to as an analog total gain) that includes the gain of the image pickup device and is provided until the photoelectric conversion output is A/D converted, is GD. In a case where the post-stage circuits are designed in accordance with the set value (the target value) GD, when the analog total gain is varied on the minimum value GL side, an image to be acquired is darkened. In contrast, when the analog total gain is varied on the maximum value GH side, the image to be acquired is brightened but S/N is disadvantageously deteriorated.

Further, it is necessary for the image pickup device to be used in a range (a linear region) in which the output is linearly changed with respect to an exposure amount. In addition, in the case where the image pickup signal has a maximum value in the linear region, when the gains are set to cause the amplified image pickup signal to have a value of a full input range of the A/D converter, the output of the image pickup device can be effectively used. In this case, when the gains of the respective analog amplifiers are set by assuming that the analog total gain is varied on the maximum value GH side, a region beyond the linear region does not appear in a video but a range allocated to the linear region is decreased to deteriorate the image quality. In contrast, when the gains of the respective analog amplifiers are set by assuming that the analog total gain is varied on the minimum value GL side, a predetermined region in which the output level is on the maximum value side of the linear region exceeds the input range of the A/D converter. This causes rough fixed pattern noise (saturation roughness), and the image quality is accordingly deteriorated. The fixed pattern noise indicates appearance, in the video, of a region in which an image pickup signal with respect to the light amount becomes non-linear for each pixel.

In other words, in the case where the analog total gain is varied on the minimum value GL side, the image is darkened. In addition, the gain setting is performed by assuming the variation, the image quality is also deteriorated. In contrast, in the case where the analog total gain is varied on the maximum value GH side, S/N is deteriorated. In addition, when the gain setting is performed by assuming the variation, the dynamic range is decreased and the image quality is accordingly deteriorated.

As mentioned above, variation of the analog total gain from the design value causes disadvantages such as deterioration of the image quality. When the size of the image pickup device is relatively large and the image pickup signal level is relatively large even in this case, the gains necessary as the analog total gain may be relatively small Therefore, since the variation of the gain is small, deterioration of the image quality is not remarkable and the problem is relatively small.

When the size of the image pickup device is decreased due to downsizing and the image pickup signal level is also decreased, and the negative gain in transmission is increased due to decrease in diameter of the cable, however, the gains necessary as the analog total gain is increased and variation is accordingly increased. Therefore, the above-described disadvantages become prominent.

Therefore, in the present embodiment, the analog total gain of the analog amplifiers on the way from the photoelectric conversion output of the image pickup device to the digital conversion of the image pickup signal is calculated, and the gain adjustment is so performed as to return the gain varied by individual difference, to the design value GD, on the basis of the calculation result. In other words, image quality is improved by making the sum (hereinafter, referred to as the total gain) of the analog total gain and the gain obtained through the gain adjustment (hereinafter, referred to as the adjustment gain) coincident with the design value GD, irrespective of downsizing, decrease in diameter, and the like. Note that the adjustment gain may be added to the analog signal before the A/D conversion or may be added to the digital signal after the A/D conversion.

In FIG. 1, the endoscope apparatus 1 includes an endoscope 10 and a video processor 50. An image pickup device 11 that is configured of, for example, CCD is provided at a distal end of an insertion portion of the endoscope 10. Illumination light emitted from an unillustrated light source is reflected by an object, and reflected light enters the image pickup device 11 through an unillustrated optical system provided at the distal end of the insertion portion. An optical image of the object is formed on an image pickup surface of the image pickup device 11 by the optical system. The image pickup device 11 photoelectrically converts the light entering each pixel. An electric signal obtained through the photoelectric conversion is outputted as an image pickup signal through the floating diffusion section 1 and the imager built-in amplifier 2 in FIG. 2.

The image pickup signal provided from the image pickup device 11 is transmitted to the proximal end side of the endoscope through the cable 3. The cable 3 is inserted into the endoscope 10 and an unillustrated universal cable, and the image pickup signal is transmitted to, for example, a substrate 13 provided inside a connector of the universal cable. The connector is connected to the video processor 50, which electrically connects the circuits mounted on the substrate 13 to the video processor 50.

The preamplifier 4, an AFE (analog front end) 15, and a FPGA (field programmable gate array) 16 are configured inside the substrate 13. The preamplifier 4 amplifies the image pickup signal with the preamplifier gain Gp, and provides the amplified image pickup signal to the AFE 15.

The image pickup signal provided from the preamplifier 4 is provided to a CDS (correlation double sampling) amplifier 21 in the AFE 15. The CDS amplifier 21 performs correlation double sampling processing on the provided analog signal to add a predetermined gain to the provided analog signal, and provides the resultant analog signal to the AGC circuit 22. The AGC circuit 22 adds a predetermined gain to an output signal of the CDS amplifier 21, and then outputs the resultant signal to the A/D converter 6. The variable amplifier 5 of FIG. 2 is configured of the CDS amplifier 21 and the AGC circuit 22.

The respective gains of the CDS amplifier 21 and the AGC circuit 22 are set by a setting section 24. The respective gains of the CDS amplifier 21 and the AGC circuit 22 are variable, and the sum of the gains of the circuits corresponds to the variable gain Gv in FIG. 2. The variable gain Gv is set to a value that is used to set the output signal of the AGC circuit 22 to a level corresponding to the input range of the A/D converter 6.

The A/D converter 6 converts the provided image pickup signal into a digital image pickup signal, and outputs the digital image pickup signal. The digital image pickup signal (the picked-up image) from the A/D converter 6 is supplied to the FPGA 16. A video processing section 30, a timing generator (TG) 48, and a driving signal generation section 49 are configured in the FPGA 16. The TG 48 generates various kinds of signals and provides the signals to the video processing section 30 and the driving signal generation section 49. The various kinds of signals include clock necessary for driving each section of the FPGA 16, and the like. The driving signal generation section 49 receives the output signal of the TG 48 to generate a clock and various kinds of driving signals necessary for operation of the image pickup device 11, and supplies the clock and the driving signals to the image pickup device 11.

The image pickup signal is provided from the A/D converter 6 to a black floating correction section 35 of the FPGA 16. The black floating correction section 35 receives a black floating correction value from a black floating correction value calculation section 41 described later, and corrects a black level of the image pickup signal with use of the black floating correction value, thereby removing an offset component of the video. An output signal of the black floating correction section 35 is provided to a gain correction section 36.

In the present embodiment, the gain correction section 36 is configured of a digital amplifier, and receives an adjustment gain GB from a gain correction value recording section

45 described later and adds the adjustment gain GB to the provided image pickup signal. In other words, the gain correction section 36 performs the gain adjustment to make the total gain of the image pickup signal coincident with the design value (the target value) GD. An output of the gain correction section 36 is supplied to a digital gain section 37. The digital gain section 37 adds a predetermined gain to the provided image pickup signal, and provides the resultant signal to a video output section 38. The video output section 38 performs predetermined video processing on the provided image pickup signal to generate a video signal, and provides the video signal to the video processor 50.

In the present embodiment, the adjustment gain GB is calculated by a correction value calculation section 40. The correction value calculation section 40 includes the black floating correction value calculation section 41, a memory section 42, and an adjustment gain calculation section 43. The memory section 42 serving as a memory section sequentially receives the image pickup signals (the picked-up images) from the A/D converter 6, and stores the image pickup signals. The black floating correction value calculation section 41 receives the picked-up image from the A/D converter 6 and the memory section 42, calculates, through a method described later, the offset component of the video that is to be used for the black floating correction, and provides the offset component as the black floating correction value to the black floating correction section 35.

The adjustment gain calculation section 43 receives the output signals from the black floating correction value calculation section 41 and the memory section 42, calculates the adjustment gain GB through a method described later, and provides a calculation result to the gain correction value recording section 45. The gain correction value recording section 45 may be configured of a non-volatile memory such as a flash memory, and records the provided adjustment gain GB and provides the adjustment gain GB to the gain correction section 36.

Note that a parameter recording section 32 is provided in the video processing section 30. The parameter recording section 32 holds parameters to determine the variable gain Gv of the CDS amplifier 21 and the AGC circuit 22. A parameter setting section 31 reads the parameters held by the parameter recording section 32 to determine the variable gain Gv, and provides, to the setting section 24 of the AFE 15, a set value to set the variable gain Gv. The setting section 24 receives the set value to set the variable gain Gv, and sets the respective gains of the CDS amplifier 21 and the AGC circuit 22 on the basis of the set value.

(Method of Calculating Analog Total Gain)

The average number of electrons of the signal generated through the photoelectric conversion in the image pickup device 11 is denoted by Nsig. An average value μ of the number of electrons of the signal is obtained by multiplying the average number of electrons Nsig by a gain value G, as represented by the following equation (1).

$$Nsig \times G = \mu \quad (1)$$

The average number of electrons Nsig is mixed with dark-time noise and light shot noise. The dark-time noise is noise that occurs irrespective of presence or absence of an amount of light entering the image pickup device and has a relatively constant level. The light shot noise is noise having a level that is varied according to the amount of the light entering the image pickup device. In other words, relationship of the following equation (2) is established for a signal output standard deviation σ by the light shot noise, according to Poisson distribution.

$$Nsig^{1/2} \times G = \sigma$$

$$Nsig \times G^2 = \sigma^2 \quad (2)$$

The following equation (3) is established from the above equation (2).

$$\mu \times G = \sigma^2$$

$$G = \sigma^2/\mu \quad (3)$$

Even when the gains are sequentially added to the output of the image pickup device, the relationship of the above equation (3) is not changed. Therefore, the analog total gain is determined by the above equation (3). The above equation (3), however, is established only for the light shot noise, and it is necessary to consider a component of the dark-time noise. Therefore, since the light shot noise is not included in the dark time in calculation of the standard deviation σ by the above equation (3), the component of the dark-time noise is removed by subtracting dark-time standard deviation σdark from bright-time standard deviation σlight including the light shot noise, and then calculation of the above equation (3) is performed.

$$\sigma^2 = \sigma light^2 - \sigma dark^2 \quad (4)$$

As mentioned above, to remove the component of the dark-time noise, the image signals of at least two frames are necessary for each of the bright time and the dark time. For example, the fixed pattern noise occurs due to an offset component generated in a column component, or the like. To remove the fixed pattern noise, it is sufficient to perform subtraction between the two frames. Accordingly, in the present embodiment, the analog total gain is calculated with use of the picked-up images of a total four frames of two frames at the bright time and two frames at the dark time.

The correction value calculation section 40 stores, in the memory section 42, the image pickup signals of the total four frames of the two frames at the bright time and the two frames at the dark time. The black floating correction value calculation section 41 determines the offset component of the video from an average difference value of two frames at the dark time, and provides the offset component as the black floating correction value to the black floating correction section 35 and the adjustment gain calculation section 43. The adjustment gain calculation section 43 determines an average value of the light shot noise and the signal component at the bright time, with use of the image pickup signals of the total four frames at the bright time and the dark time, and then calculates the analog total gain from the above equation (3). The adjustment gain calculation section 43 calculates, as the adjustment gain GB, a difference between the calculated analog total gain and the target total gain (the design value) GD.

Figure 4:
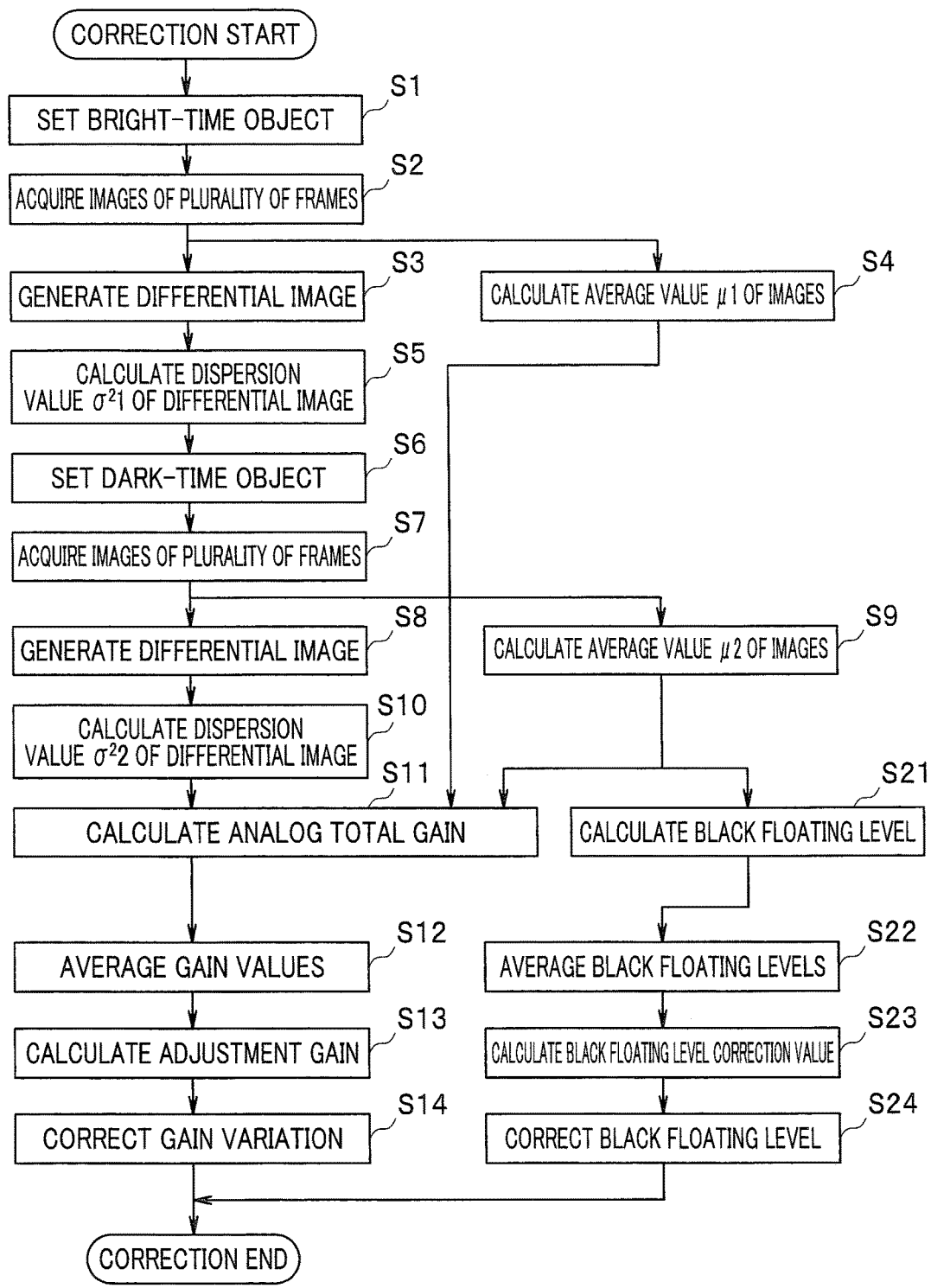
FIG. 4 is a flowchart to explain black floating correction and gain adjustment by a correction value calculation section 40.

Next, operation of the embodiment having the above-described configuration is described with reference to FIG. 4 and FIG. 5. FIG. 4 is a flowchart to explain the black floating correction and the gain adjustment by the correction value calculation section 40.

In the present embodiment, the calculation of the adjustment gain by the gain adjustment unit may be performed, for example, at the time when the endoscope 10 is shipped from a factory. As described above, the picked-up images of two frames at the bright time and the picked-up images of two frames at the dark time are used to calculate the adjustment gain. To acquire the picked-up images of two frames at the bright time, a bright-time object is set at step S1 in FIG. 4. As the bright-time object, for example, a white cap for white balance adjustment that is attached to the distal end of the insertion portion of the endoscope may be used. At next step S2, picked-up images of a plurality of frames are acquired. For example, picked-up images of two frames are successively photographed to acquire the picked-up images of two frames at the bright time. In addition, in a case where the calculated adjustment gains are averaged to improve calculation accuracy, the picked-up images of two frames at the bright time may be acquired several times.

The image pickup signals of the plurality of frames acquired by the image pickup device 11 are supplied to the preamplifier 4 of the substrate 13 through the cable 3. Each of the image pickup signals is amplified by the preamplifier 4, and the amplified image pickup signal is provided to the AFE 15. The CDS amplifier 21 and the AGC circuit 22 of the AFE 15 amplifies the provided image pickup signal according to the set value of the setting section 24, and provides the amplified image pickup signal to the A/D converter 6. The photoelectric conversion output of the image pickup device 11 at the bright time is added with the imager gain Gi, the cable gain Gk, the preamplifier gain Gp, and the variable gain Gv, and the resultant is then supplied to the A/D converter 6.

The A/D converter 6 converts the provided image pickup signal into a digital image pickup signal, and provides the digital image pickup signal to the video processing section 30 in the FPGA 16. The digital image pickup signal is provided to the black floating correction section 35, and the black floating correction value calculation section 41 and the memory section 42 of the correction value calculation section 40.

The adjustment gain calculation section 43 determines, for example, a difference between the images of the successive two frames (step S3). The fixed pattern noise contained in the picked-up bright-time image is removed through the difference calculation. The adjustment gain calculation section 43 calculates a dispersion value $\sigma^2 1$ of the image of the differential result (a differential image) (step S5). Although the fixed pattern noise has been removed from the differential image, dark current noise and random noise containing the light shot noise are still contained in the differential image. The dispersion value $\sigma^2 1$ is a dispersion value of the light shot noise influenced by the dark current noise.

In addition, the adjustment gain calculation section 43 calculates an average value of the images of the plurality of frames picked up at the bright time, at step S4. The dark current noise and the random noise containing the light shot noise are removed through the averaging. Accordingly, a signal level µ1 of the bright-time image is determined through the averaging processing at step S4.

Next, to acquire the images of two frames at the dark time, a dark-time object is set (step S6). For example, images are picked up while an incident surface of the image pickup device 11 on the distal end of the endoscope is shielded from light. At next step S7, images of a plurality of frames are acquired. For example, images of two frames are successively photographed to acquire images of two frames at the dark time. In addition, in a case where the calculated adjustment gains are averaged to improve calculation accuracy, the images of two frames at the dark time may be acquired several times.

The image pickup signals of the plurality of frames acquired by the image pickup device 11 are supplied to the A/D converter 6 through the cable 3, the preamplifier 4, the CDS amplifier 21, and the AGC circuit 22. As mentioned above, the photoelectric conversion output of the image pickup device 11 at the dark time is added with the imager gain Gi, the cable gain Gk, the preamplifier gain Gp, and the variable gain Gv, and the resultant is then supplied to the A/D converter 6.

The A/D converter 6 converts the provided image pickup signal into a digital image pickup signal. The digital image pickup signal is provided to the black floating correction section 35, and the black floating correction value calculation section 41 and the memory section 42 of the correction value calculation section 40. The adjustment gain calculation section 43 determines, for example, a difference between the images of successive two frames (step S8). The differential result is a dark-time image from which the fixed pattern noise has been removed. The adjustment gain calculation section 43 calculates a dispersion value $\sigma^2 2$ of the image of the differential result (the differential image) at step S10. The dispersion value $\sigma^2 2$ is a dispersion value of the dark current noise with the light shot noise having the level of zero. Note that the standard deviation may be used to calculate the analog total gain, in place of the dispersion value.

In addition, the black floating correction value calculation section 41 and the adjustment gain calculation section 43 calculate an average value of the images of the plurality of frames picked up at the dark time, at step S9. The dark current noise is removed through the averaging. Accordingly, a signal level µ2 of the dark-time image is determined through the averaging processing at step S9. The signal level µ2 is thereafter used in both of the black floating correction value calculation section 41 and the adjustment gain calculation section 43, and may be determined by one of the calculation sections and provided to the other calculation section.

Note that the averaging processing at step S9 is to acquire the signal level of the dark-time image, namely, to acquire the offset component of the video. The black floating correction value calculation section 41 determines the black floating level from the signal level µ2 determined through the averaging processing of the dark-time image. For example, the black floating correction value calculation section 41 may use, as the offset component, the signal level µ2 as is.

The black floating correction value calculation section 41 may determine the black floating level from the images of two frames several times, and may average the determined black floating levels in order to improve the black floating correction accuracy (step S22). The black floating correction value calculation section 41 calculates the black floating level correction value for correction of the determined black floating level, and provides the black floating level correction value to the black floating correction section 35 (step S23). In the actual picking up of the images, the black floating correction section 35 corrects the black floating level of the provided image with use of the black floating level correction value, and outputs the correction result.

In contrast, the adjustment gain calculation section 43 calculates the analog total gain at step S11. In other words, the adjustment gain calculation section 43 subtracts the dark-time dispersion value $\sigma^2 2$ determined at step S10 from the bright-time dispersion value $\sigma^2 1$ determined at step S5, thereby acquiring a dispersion value $\sigma^2$ of the light shot noise from which influence of the dark current noise has been removed. Moreover, the adjustment gain calculation section 43 subtracts the average value µ2 of the dark-time image determined at step S9 from the average value µ1 of the bright-time image determined at step S4, thereby acquiring an average value µ of the bright-time image. The adjustment gain calculation section 43 determines the analog total gain from the determined dispersion value $\sigma^2$ and the determined average value $\mu$, on the basis of the above equation (3).

The adjustment gain calculation section 43 may determine the analog total gain from the images of four frames several times, and may average the determined analog total gains in order to improve the correction accuracy of the gain variation (step S12). The adjustment gain calculation section 43 calculates, as the adjustment gain GB, the difference between the determined analog total gain and the target total gain (the design value) GD (step S13). The adjustment gain calculation section 43 provides and records the determined adjustment gain GB in the gain correction value recording section 45.

The adjustment gain GB that corrects variation of the respective gains of the image pickup device 11, the cable 3, the preamplifier 4, the CDS amplifier 21, and the AGC circuit 22 is stored in the correction value recording section 45 in the above-described manner, at the shipment from a factory. Note that the image pickup device 11, the cable 3, and the substrate 13 are variously combined; however, a user does not typically replace the image pickup device 11 and the cable 3 from the endoscope 10, and the replacement is performed in the factory. Accordingly, it is unnecessary for the gain correction value recording section 45 to hold a plurality of adjustment gains GB corresponding to a plurality of combinations of the image pickup device 11, the cable, and the substrate 13, and it is sufficient for the gain correction value recording section 45 to hold only the adjustment gain GB determined at the shipment from the factory.

In the actual use, the output of the black floating correction section 35 is supplied to the digital gain section 37 through the gain correction section 36. The adjustment gain GB is set by the gain correction value recording section 45, and the gain correction section 36 adds the adjustment gain GB to the output of the black floating correction section 35 and outputs the resultant. The gain correction section 36 is configured of a digital amplifier, and performs accurate gain adjustment.

Figure 5:
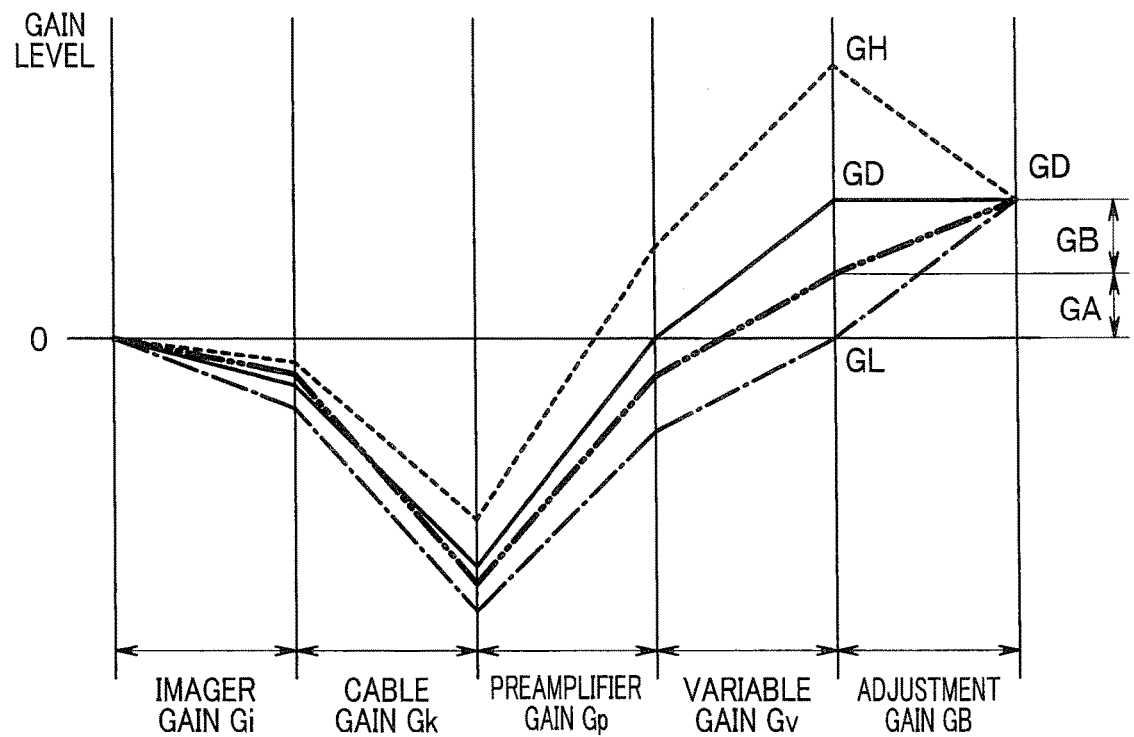
FIG. 5 is a graph to explain gain adjustment by a gain correction section 36.

FIG. 5 is a graph to explain the gain adjustment by the gain correction section 36. FIG. 5 illustrates results of the gain adjustment by an illustration method similar to the illustration method of FIG. 3, in which the horizontal axis indicates each stage of the amplifier, and the vertical axis indicates a gain. In FIG. 5, a solid line indicates change of the analog total gain according to the design values of the respective gains, a dashed line indicates the change of the analog total gain in a case where the maximum analog total gain GH is obtained, an alternate long and short dash line indicates the change of the analog total gain in a case where a minimum analog total gain GL is obtained, and an alternate long and two short dashes line (a heavy line) indicates change of the total gain derived from variation of the actual gains and the adjustment.

In the example of FIG. 5, the adjustment gain calculation section 43 calculates an analog total gain value GA. The adjustment gain calculation section 43 subtracts the analog total gain value GA from the target gain GD to calculate the adjustment gain GB. The adjustment gain GB is recorded in the gain correction value recording section 45. The gain correction section 36 adds the adjustment gain GB set by the gain correction value recording section 45 to the provided image pickup signal, and outputs the resultant signal. Therefore, the adjustment gain GB is added, after the A/D conversion, to the analog total gain GA that is to be added to the photoelectric conversion output before the A/D conversion, and the total gain accordingly becomes the target value GD.

As mentioned above, in the present embodiment, the analog total gain that is to be added on the way from the photoelectric conversion output to the A/D conversion is calculated on the basis of the light shot noise at the bright time and the average value of the signals, and the gain adjustment is performed on the basis of the calculation result such that the total gain is coincident with the design value. Since it is possible to correct the variation of the analog gain to make the total gain coincident with the target design value in the above-described manner, the image with sufficient brightness and favorable S/N is provided. In addition, since the gain design that makes the linear region of the image pickup signal coincident with the input level of the A/D converter is performable without considering the variation of the analog gain, the gain design effectively using the dynamic range of the A/D converter is performable, which makes it possible to provide the image with sufficient brightness and less deterioration of the image quality. Consequently, even if the level of the image pickup signal is decreased by downsizing and the negative gain in transmission is increased by the decrease in diameter of the cable, it is possible to offset the variation of the gain and to achieve high image quality.

Note that, in the above-described embodiment, the example in which the analog total gain before the A/D conversion is calculated and the gain adjustment is performed after the A/D conversion on the basis of the analog total gain calculated by the digital amplifiers has been described. The gain adjustment, however, may be performed with use of the analog amplifiers before the A/D conversion. In this case, the adjustment gain is varied by variation of the analog amplifiers even when the adjustment gain is set to each of the analog amplifiers. Therefore, it is necessary to perform feedback correction to make the total gain coincident with the target value.

Moreover, in the above-described embodiment, the adjustment gain is added to the analog total gain to make the total gain coincident with the target value; however, the total gain equivalent to the analog total gain may be made coincident with the target value by adjusting the gains of the respective gain generation sources that provide the analog total gain. For example, the gain of the AGC circuit in the AFE circuit may be adjusted. In this case, (the analog total gain—a gain of the AGC circuit before the gain adjustment+a gain of the AGC circuit after the gain adjustment) =the total gain is made coincident with the target value.

Incidentally, the gain adjustment unit according to the above-described embodiment includes the correction value calculation section 40, the gain correction value recording section 45, and the gain correction section 36. In the present embodiment, the example in which the gain adjustment unit is incorporated in the endoscope 10 has been described. It is sufficient, however to store the information of the adjustment gain in the gain correction value recording section 45 at the shipment from a factory of the endoscope, and it is unnecessary for the correction value calculation section 40 to be incorporated in the endoscope. In other words, it is sufficient for the endoscope to include only the gain correction value recording section 45 and the gain correction section 36.

Further, in the case where the adjustment gain is added by the analog amplifier as mentioned above, the gain correction section 36 may be omitted. In this case, for example, the parameter setting section 31 may determine the information to be provided to the setting section 24, on the basis of the information of the parameter recording section 32 and the gain correction value recording section 45.

Accordingly, it is unnecessary for the gain adjustment unit to be incorporated in the endoscope, and the gain adjustment unit may be provided inside the video processor or outside the endoscope apparatus as long as, for example, the image pickup signal is outputted from the endoscope.

Moreover, in the above-described embodiment, the example in which the picked-up images at the bright time and at the dark time are stored in the memory section 42, and statistics such as the above-described dispersion value are determined has been described. In a case where a device having sufficiently small fixed pattern noise is used as the image pickup device or in a case where the value of the analog total gain to be calculated is determined as an approximate value, however, the dispersion value and the standard deviation may be determined with use of the average value of the image before one frame because of high correlation of the average value of the images. Therefore, even in the case where the memory section 42 is omitted, it is possible to calculate the analog total gain by the adjustment gain calculation section 43 by taking in the statistics such as the dispersion value and the standard deviation obtained from the picked-up images. Further, a memory that holds such statistics may be additionally provided.

In addition, the calculation processing of the adjustment gain by the gain adjustment unit is performable through software processing by causing a computer to execute programs in which the calculation processing of the adjustment gain is described.

The present invention is not limited to the above-described embodiment, and is implemented by modifying the components without departing from the scope of the invention in execution stage. Moreover, various inventions may be made through appropriate combination of the plurality of components disclosed in the above-descried embodiment. For example, some of the components described in the embodiment may be removed.

What is claimed is:

1. A gain adjustment unit, comprising:
an analog total gain calculation section configured to calculate a total sum of analog gains on a way from photoelectric conversion output of an image pickup device to input of an analog/digital conversion circuit with use of picked-up images provided from the analog/digital conversion circuit, the analog/digital conversion circuit being configured to convert an output of an analog processing section into a digital signal, the analog processing section being configured to transmit and amplify an image pickup signal from the image pickup device, the image pickup device being provided at an insertion portion of an endoscope;
an adjustment gain calculation section configured to determine, as an adjustment gain, a difference between a target value of a total sum of gains on the way from the photoelectric conversion output of the image pickup device to the input of the analog/digital conversion circuit and the total sum of the analog gains, and output information of the adjustment gain to adjust an analog gain of the endoscope; and
a memory section configured to take in the picked-up image from the analog/digital conversion circuit,
wherein the analog total gain calculation section calculates the total sum of the analog gains with use of the picked-up image based on an output of the image pickup device at bright time and the picked-up image based on an output of the image pickup device at dark time, among the picked-up images held by the memory section.

2. The gain adjustment unit according to claim 1, wherein the analog total gain calculation section determines light shot noise of the image pickup device on a basis of statistics of the picked-up bright-time images and statistics of the picked-up dark-time images, determines a level of the picked-up bright-time image on a basis of an average value of the picked-up bright-time images and an average value of the picked-up dark-time images, and calculates the analog total gain on a basis of the determined light shot noise and the level of the picked-up image.

3. The gain adjustment unit according to claim 2, wherein the statistics are standard deviation or dispersion values.

4. The gain adjustment unit according to claim 1, wherein
the memory section holds the picked-up images of two frames or more at the bright time and the picked-up images of two frames or more at the dark time, and
the analog total gain calculation section removes fixed pattern noise with use of a difference between the picked-up images of two frames or more at the bright time, and removes the fixed pattern noise with use of a difference between the picked-up images of two frames or more at the dark time.

5. An endoscope, comprising:
a recording section configured to record information of the adjustment gain that is provided from the gain adjustment unit according to claim 1; and
a digital amplifier configured to add the adjustment gain to an output of the analog/digital conversion circuit, on a basis of the information of the adjustment gain.

6. The endoscope according to claim 5, further comprising a gain adjustment unit that includes an analog total gain calculation section and an adjustment gain calculation section, the analog total gain calculation section being configured to calculate a total sum of analog gains on a way from photoelectric conversion output of an image pickup device to input of an analog/digital conversion circuit with use of picked-up images provided from the analog/digital conversion circuit, the analog/digital conversion circuit being configured to convert an output of an analog processing section into a digital signal, the analog processing section being configured to transmit and amplify an image pickup signal from the image pickup device, the image pickup device being provided at an insertion portion of an endoscope, and the adjustment gain calculation section being configured to determine, as an adjustment gain, a difference between a target value of a total sum of gains on the way from the photoelectric conversion output of the image pickup device to the input of the analog/digital conversion circuit and the total sum of the analog gains, and to output information of the adjustment gain to adjust an analog gain of the endoscope.

7. An endoscope apparatus, comprising:
the endoscope according to claim 5; and
a video processor configured to receive an output of the endoscope and to perform predetermined image processing on the output, wherein
the video processor includes a gain adjustment unit that includes an analog total gain calculation section and an adjustment gain calculation section, the analog total gain calculation section being configured to calculate a total sum of analog gains on a way from photoelectric conversion output of an image pickup device to input of an analog/digital conversion circuit with use of picked-up images provided from the analog/digital conversion circuit, the analog/digital conversion circuit being configured to convert an output of an analog processing section into a digital signal, the analog processing section being configured to transmit and amplify an image pickup signal from the image pickup device, the image pickup device being provided at an insertion portion of an endoscope, and the adjustment gain calculation section being configured to determine, as an adjustment gain, a difference between a target value of a total sum of gains on the way from the photoelectric conversion output of the image pickup device to the input of the analog/digital conversion circuit and the total sum of the analog gains, and to output information of the adjustment gain to adjust an analog gain of the endoscope.

8. An endoscope, comprising:

a recording section configured to record information of the adjustment gain that is provided from the gain adjustment unit according to claim 1; and an analog gain control section configured to control a gain of the analog processing section to add the adjustment gain to the total sum of the analog gains, on a basis of the information of the adjustment gain.

* * * * *